US00PP28581P3

(12) United States Plant Patent
Fazio et al.

(10) Patent No.: US PP28,581 P3
(45) Date of Patent: Oct. 31, 2017

(54) APPLE TREE ROOTSTOCK NAMED 'G.213'

(50) Latin Name: ***Malus domestica*×*Malus robusta***
Varietal Denomination: G.213

(71) Applicants: Cornell University, Ithaca, NY (US); The United States of America, as Represented by the Secretary of Agriculture, Washington, DC (US)

(72) Inventors: Gennaro Fazio, Geneva, NY (US); Herb Aldwinckle, Geneva, NY (US); James Cummins, Alcoa, TN (US); Terence Robinson, Geneva, NY (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 138 days.

(21) Appl. No.: 14/756,708

(22) Filed: Sep. 30, 2015

(65) Prior Publication Data

US 2017/0094854 P1 Mar. 30, 2017

(51) Int. Cl.
*A01H 5/08* (2006.01)

(52) U.S. Cl.
USPC ..... Plt./161

(58) Field of Classification Search
USPC ..... Plt./174, 161
See application file for complete search history.

*Primary Examiner* — Susan McCormick Ewoldt
*Assistant Examiner* — Karen Redden
(74) *Attorney, Agent, or Firm* — Morrison & Foerster LLP

(57) ABSTRACT

The present invention relates to a new and distinct variety of apple tree *Malus domestica*×*Malus robusta* hybrid named 'G.213'. 'G.213' is useful in that it can be propagated clonally and used as a rootstock or root system for apple trees as well as for interstems of apple trees. The new variety is a dwarfing rootstock that is resistant to fire blight (*Erwinia amylovora*) and crown rot (*Phytophthora cactorum*).

7 Drawing Sheets

STATEMENT REGARDING FEDERAL FUNDING

This invention was made with United States government support under a United States Department of Agriculture—Agricultural Research Station Cooperative Research and Development Agreement, Sponsor's Contract Number 58-3K95-4-1668-M. The government has certain rights in the invention.

Genus and species: *Malus domestica*×*Malus robusta* hybrid.

Variety denomination: 'G.213'.

BACKGROUND OF THE NEW PLANT AND COMPARISONS

I. Field & Utility Summary

The present invention relates to a new and distinct variety of apple tree. The apple tree is particularly useful in that it can be propagated clonally and used as a rootstock or root system for apple trees as well as for interstems of apple trees. The new variety is a dwarfing rootstock that is resistant to fire blight and crown rot. It is precocious and highly productive.

II. Cultivation Summary

'G.213' originated from a planned cross in 1976 in Geneva, N.Y.

III. Comparisons

The seed parent *Malus domestica* hybrid 'Ottawa 3' (not patented) is a dwarfing rootstock, i.e., trees grown on this rootstock are 25 to 35 percent the size of a standard self-rooted seedling apple tree. 'Ottawa 3' is well known to induce precocity to the scion (i.e., the ability to induce early, reproductive development on grafted scions) and has good yield efficiency (i.e., the ability to produce many apples per square centimeter of trunk). 'Ottawa 3' produces no spines in stool bed clonal propagation, it is winter hardy, but susceptible to the woolly apple aphid (*Eriosoma lanigerum*), to fire blight (*Erwinia amylovora*), and to the specific replant disease complex.

The pollen parent *Malus robusta* 'Robusta 5' (not patented) is a non-dwarfing rootstock, i.e. trees on this rootstock grow to the same size of a standard self-rooted apple tree. 'Robusta 5' does not induce precocity to the scion and is not yield efficient. Juvenile plants and young stool propagules of 'Robusta 5' produce many spines. 'Robusta 5' is resistant to fire blight and powdery mildew (*Podusphaera leoucotricha*), and is immune to the woolly apple aphid. 'Robusta 5' breaks buds very early in the spring and is winter hardy. Further, 'Robusta 5' has shown tolerance to the specific replant disease complex.

The 'G.213' apple rootstock of the present invention has a combination of qualities that distinguishes it from its parental plants (i.e., 'Ottawa 3' and 'Robusta 5'). For example, although 'Ottawa 3' is susceptible to the woolly apple aphid, 'G.213' has resistance to it. In addition, 'G.213' has a yield efficiency similar to 'Ottawa 3'. 'G.213' has dwarfing properties derived from 'Ottawa 3', and belongs to the same dwarfing vigor class as its dwarfing parent (i.e., 'Ottawa 3'), allowing trees grafted on this rootstock to grow 25 to 35 percent of standard self-rooted apple tree seedlings. Specifically, 'G.213' is in the same dwarfing vigor class as industry standard 'Mailing 9' (not patented). 'G.213' shares further similarities with 'Ottawa 3' in that they both induce precocity to the scion and are winter hardy.

With regard to its 'Robusta 5' parent, 'G.213' is distinguishable in that it is a dwarfing rootstock and is yield efficient, while 'Robusta 5' is not. However, like 'Robusta 5', 'G.213' is resistant to fire blight and the woolly apple aphid (*Eriosoma lanigerum*), and produces some spines (sylleptic small branches) at the base of clonally propagated stool bed shoots. In addition, 'G.213' has been shown to have some tolerance to the replant disease complex.

As discussed above, 'G.213' is most similar to 'Mailing 9' in terms of dwarfing class. However, 'G.213' is resistant to fire blight and woolly apple aphid whereas 'Mailing 9' and other rootstocks in its market class are not.

Comparison of 'G.213' with 'G.814' (U.S. Plant Pat. No. 27,643). 'G.213' is distinguishable from 'G.814' in that it has leaves that are epinastic (leaves having downward curvature), while 'G.814' has leaves that are not epinastic and are fairly straight with the exception of last centimeter of tip which may recurve. In addition, 'G.213' has three to five waves per edge of leaves, while 'G.814' has one to three waves per edge of leaves. Further, 'G.213' has an axillary angle of leaves (angle of leaf tip to stem) that is droopy, whereas 'G.814' has a medium upright axillary angle of leaves. Moreover, 'G.213' is resistant to woolly apple aphids, while 'G.814' is susceptible to wooly apple aphids. Further distinguishing features are apparent from the comparison between 'G.213' and 'G.814' depicted in FIG. 8.

Comparison of 'G.213' with 'G.210' (U.S. Plant Pat. No. 23,337). 'G.213' is distinguishable from 'G.210' in that it has leaves that are epinastic (leaves having downward curvature), while 'G.210' has leaves that are not epinastic and are fairly straight with the exception of last centimeter of tip which may recurve. Further, 'G.213' has an axillary angle of leaves (angle of leaf tip to stem) that is droopy, whereas 'G.210' has a medium axillary angle of leaves. Further distinguishing features are apparent from the comparison between 'G.213' and 'G.210' depicted in FIG. 8.

Comparison of 'G.213' with 'G.890' (U.S. Plant Pat. No. 23,327). 'G.213' is distinguishable from 'G.890' in that it has leaves that are epinastic (leaves having downward curvature), while 'G.890' has leaves with slight curvature. In addition, 'G.213' has three to five waves per edge of leaves, while 'G.890' has one to two waves per edge of leaves. Further, 'G.213' has an axillary angle of leaves (angle of leaf tip to stem) that is droopy, whereas 'G.890' has a medium flat axillary angle of leaves. Moreover, 'G.213' has a leaf flatness (the openness of the leaf where the blade is divided longitudinally in two halves by the main venation) that is concave, while 'G.890' has a medium flat leaf flatness. Further distinguishing features are apparent from the comparison between 'G.213' and 'G.890' depicted in FIG. 8.

Comparison of 'G.213' with 'G.214' (U.S. Plant Pat. No. 23,516). 'G.213' is distinguishable from 'G.214' in that it has leaves that are epinastic (leaves having downward curvature), while 'G.214' has leaves with medium epinasty. In addition, 'G.213' has three to five waves per edge of leaves, while 'G.214' has one to three waves per edge of leaves. Further, 'G.213' has an axillary angle of leaves (angle of leaf tip to stem) that is droopy, whereas 'G.214' has a medium flat axillary angle of leaves. Further distinguishing features are apparent from the comparison between 'G.213' and 'G.214' depicted in FIG. 8.

Comparison of 'G.213' with 'G.969' (U.S. Plant Pat. No. 24,073). 'G.213' is distinguishable from 'G.969' in that it has leaves that are epinastic (leaves having downward curvature), while 'G.969' has leaves with slight curvature. In addition, 'G.213' has three to five waves per edge of leaves, while 'G.969' has one to two waves per edge of leaves. Further, 'G.213' has an axillary angle of leaves (angle of leaf tip to stem) that is droopy, whereas 'G.969' has a medium flat axillary angle of leaves. Moreover, 'G.213' has a leaf flatness (the openness of the leaf where the blade is divided longitudinally in two halves by the main venation) that is concave, while 'G.969' has a medium flat leaf flatness. Further distinguishing features are apparent from the comparison between 'G.213' and 'G.969' depicted in FIG. 8.

Comparison of 'G.213' with 'G.935' (U.S. Plant Pat. No. 17,063). 'G.213' is distinguishable from 'G.935' in that while both have leaves that are epinastic (leaves having downward curvature), 'G.935' has a much more pronounced curvature in mature leaves than 'G.213'. In addition, 'G.213' has three to five waves per edge of leaves, while 'G.935' has one to two waves per edge of leaves. Moreover, 'G.213' is resistant to woolly apple aphids, while 'G.935' is susceptible to woolly apple aphids. Further distinguishing features are apparent from the comparison between 'G.213' and 'G.935' depicted in FIG. 8.

IV. Breeding History

In the spring of 1976, pollen from a *Malus robusta* 'Robusta 5' apple tree was applied to emasculated flowers of a *Malus domestica* hybrid 'Ottawa 3' in Geneva, N.Y. In the fall of 1976, seeds resulting from this pollination were extracted from mature fruit derived from this cross. In the winter of 1976-77, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1977, each of the transplanted seedlings was inoculated with approximately 106 colony forming units of the Ea 273 strain of the fire blight bacterium *Erwinia amylovora* by inserting a 26-gauge hypodermic syringe needle into the shoot tip. The seedling designated as #213 was one of the survivors of this battery of inoculations from the same cross. All the surviving plants were transplanted to the nursery field (Geneva, N.Y.) in the fall of 1977 and allowed to grow side shoots for propagation/evaluation.

In 1980, 'G.213' was evaluated for rooting ability, lack of spine production, and low root brittleness in a layering bed (stool bed). In 1983, 4 finished trees with 'G.213' rootstock were planted in a first test orchard (Geneva, N.Y.) with *Malus domestica* cv. 'Northern Spy' (not patented) grafted onto this rootstock as the scion cultivar. This rootstock performed well (top 20% of many rootstocks tested) in these first test trials, and during 1990-1993 more material was propagated by stool bed and nursery to be entered into new trials at a second test orchard (Geneva, N.Y.) with *Malus domestica* cv. 'Empire' (not patented) as the scion cultivar. The 'G.213' rootstock performed well with all the scion cultivars that were tested. In August of 2002, several rootstock liners of 'G.213' were budded with 15 different scion cultivars to test graft union compatibility—the test results showed that 'G.213' was compatible with all cultivars tested.

V. Asexual Reproduction

Asexual reproduction of the 'G.213' apple rootstock has been achieved using the traditional method of clonally propagating apple rootstocks. In particular, the original seedling of the 'G.213' apple rootstock was planted in the field (Geneva, N.Y.) and allowed to develop into a "mother plant". The 'G.213' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.213' apple rootstock variety has been asexually reproduced by root cuttings, by budding and grafting onto seedling and clonal rootstocks, and by in vitro culture. Asexual reproduction by layering, root cuttings, budding, grafting, and tissue culture in Geneva, N.Y. has shown that the claimed plant reproduces true to type through successive generations of asexual reproduction.

VI. Stability

Observations of trees from these propagations indicate that all trees have proven true to type and identical in all appearances to the original tree.

SUMMARY

The present invention relates to a new and distinct variety of apple tree rootstock named 'G.213'. The 'G.213' apple tree rootstock is a dwarfing rootstock that is resistant to fire blight (*Erwinia amylovora*) and crown rot (*Phytophthora cactorum*). The 'G.213' rootstock is useful in that it can be propagated clonally and used as a rootstock or root system for apple trees as well as for interstems of apple trees. While 'G.213' rootstock is a hybrid from a cross between 'Ottawa 3' and 'Robusta 5', it is distinct from its parent cultivars in terms of dwarfing and disease resistance. The apple tree rootstock 'G.213' produces grafted trees that are 25 to 35 percent the size of self-rooted standard apple trees, it induces good precocity on the scion, and is tolerant to the replant disease complex.

BRIEF DESCRIPTION OF THE PHOTOGRAPHS

The new apple tree 'G.213' is illustrated by the accompanying photographs. The colors shown are as true as can be reasonably obtained by conventional photographic procedures. FIGS. 1, 2, 3, 4 and 6 depict photographs of one-year-old shoots from propagation beds that are at least four years old. FIGS. 5 and 7 depict photographs of plants that are about eight years old and that have mature shoots.

Figure 1:
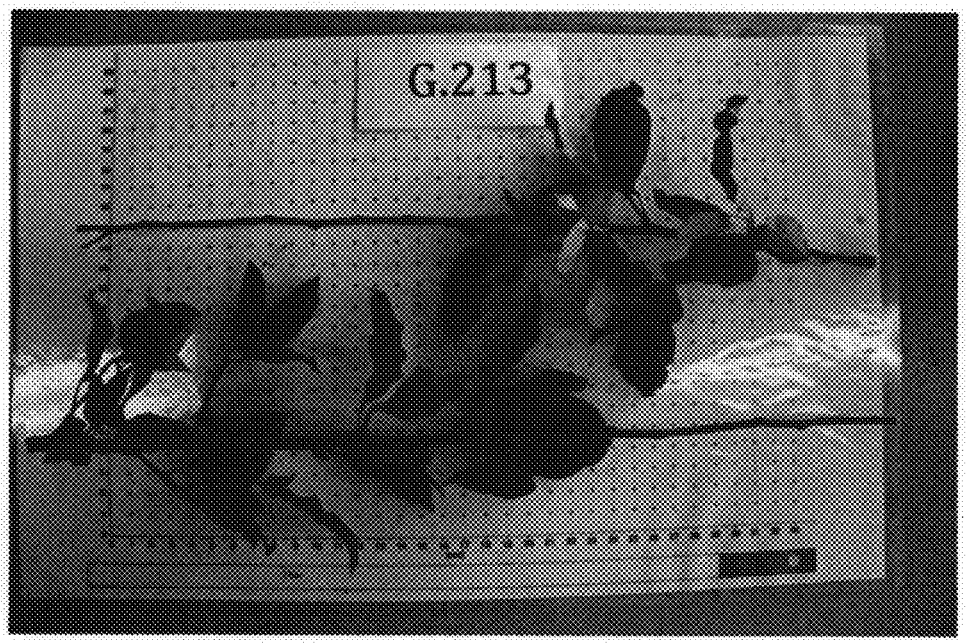
FIG. 1 shows non-dormant shoot (including, spines, buds and bark).
Figure 2:
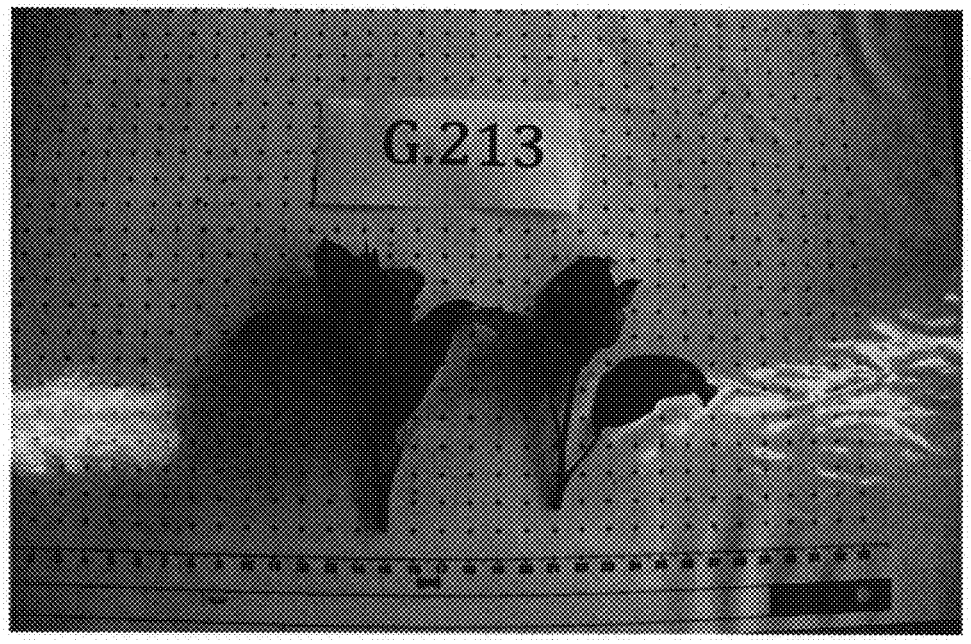
FIG. 2 shows a close-up view of a live shoot (including expanding leaves).
Figure 3:
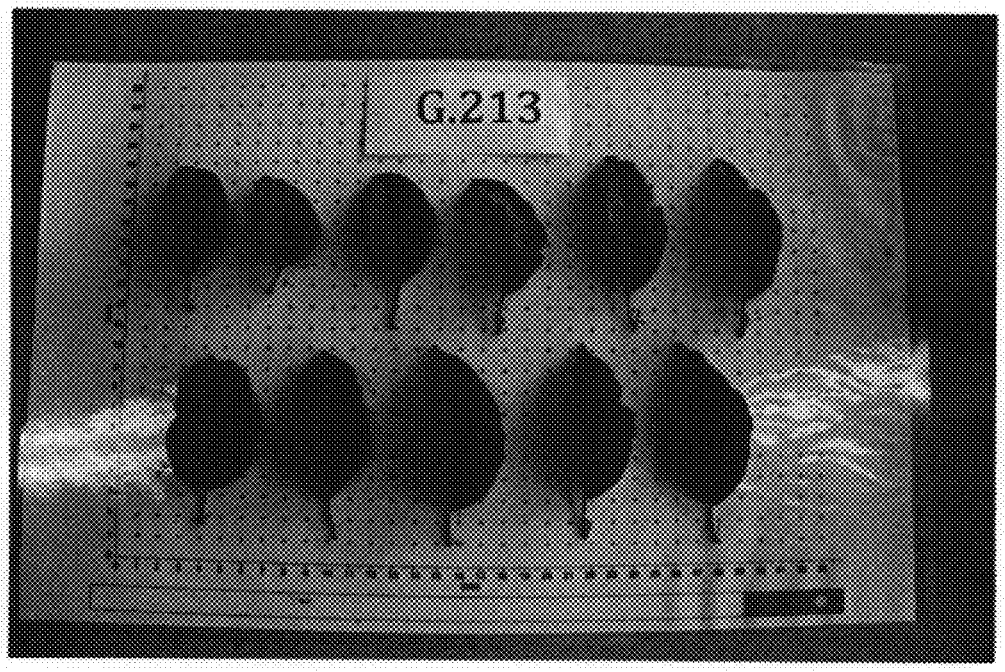
FIG. 3 shows the adaxial (upper) lamina surface of mature leaves.
Figure 4:
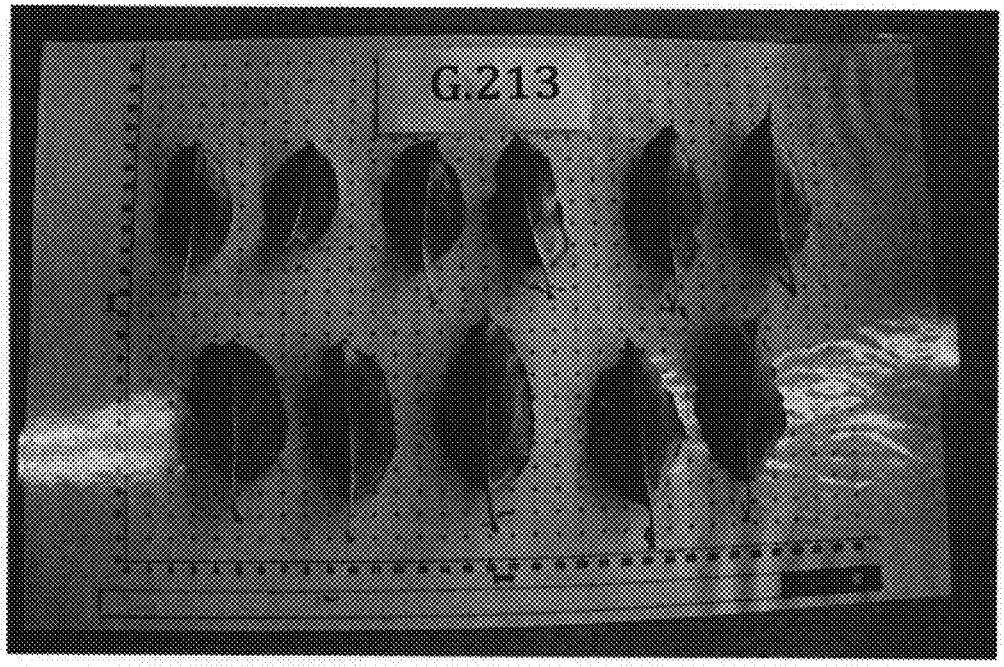
FIG. 4 shows the abaxial (lower) lamina surface of mature leaves.
Figure 5:
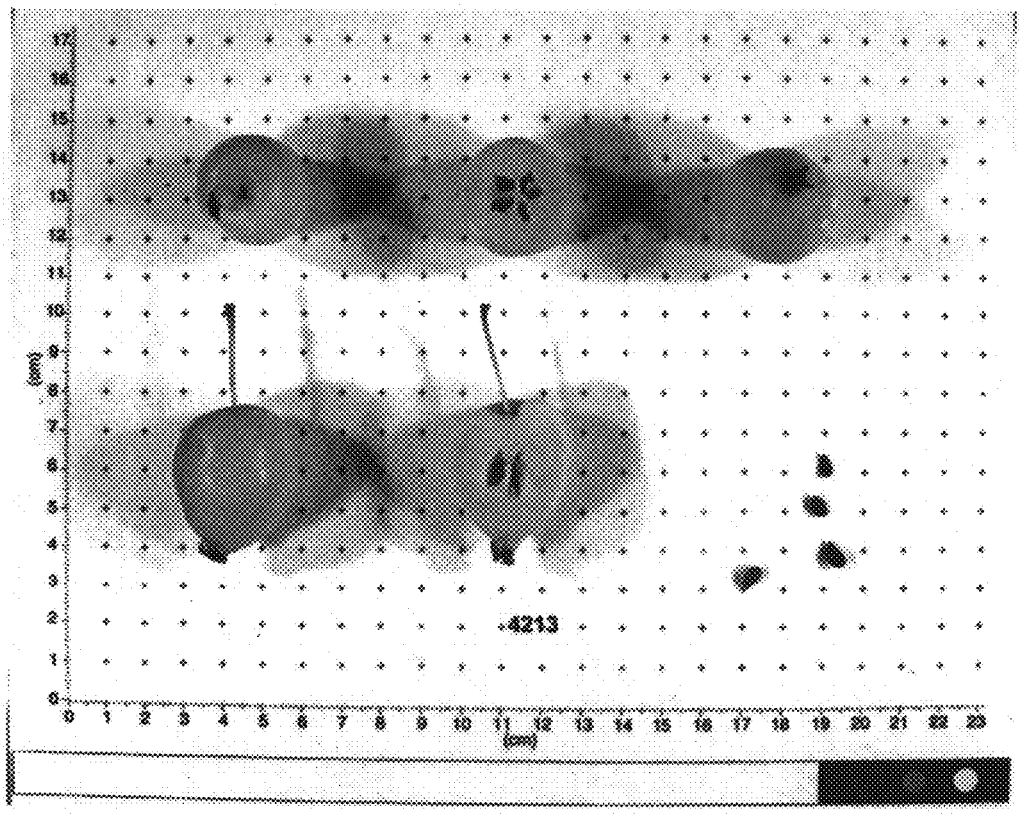
FIG. 5 shows the mature fruit.
Figure 6:
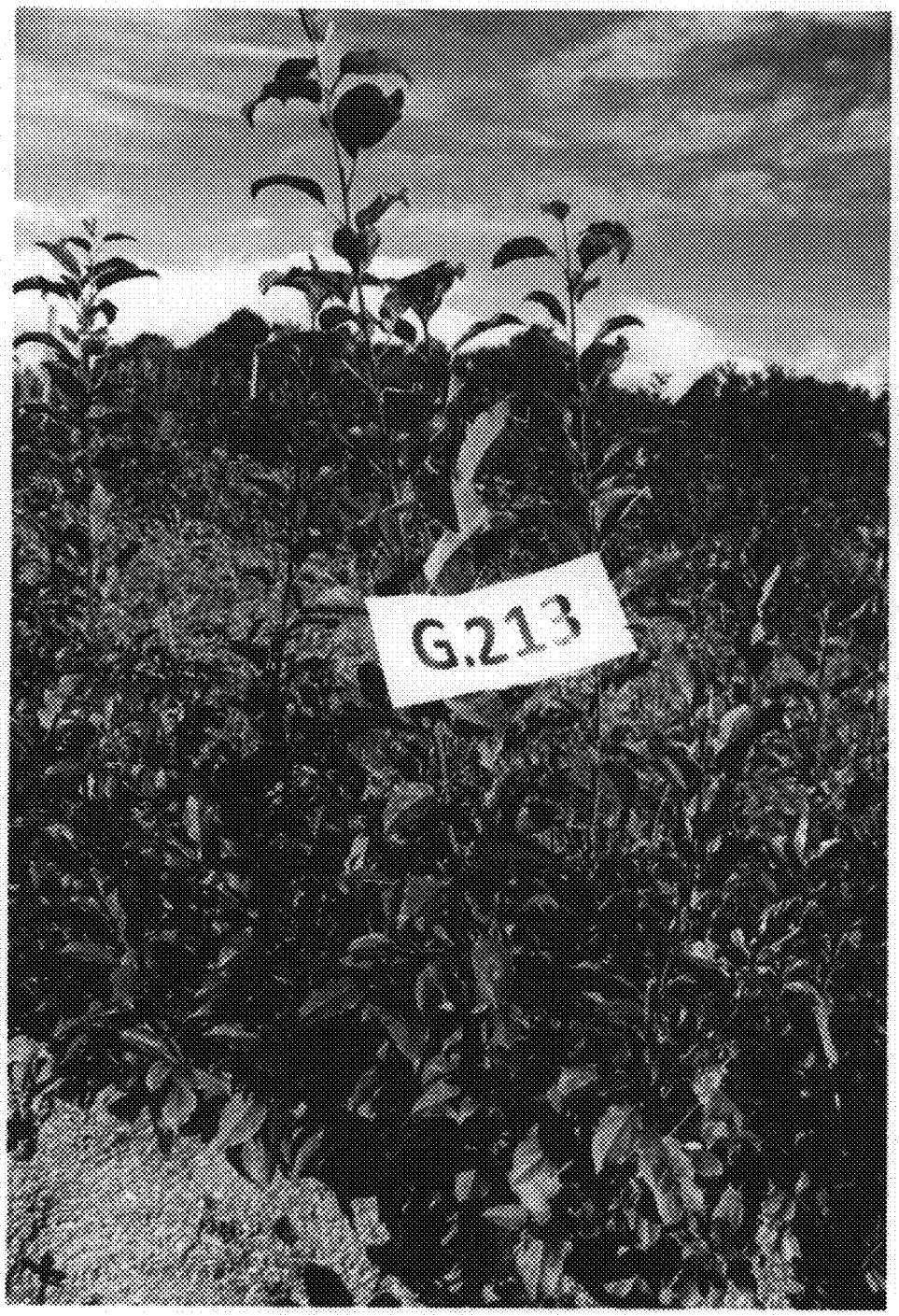
FIG. 6 shows shoots on a clonal propagation stool bed.
Figure 7:
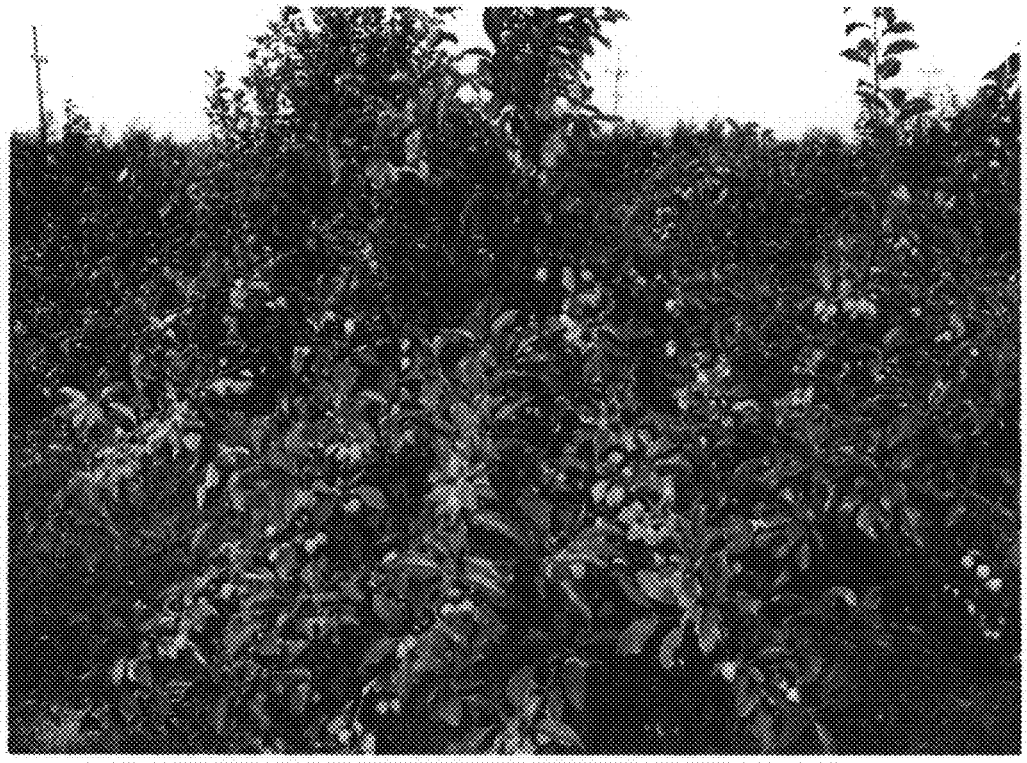
FIG. 7 shows eight-year-old trees.
Figure 8A:
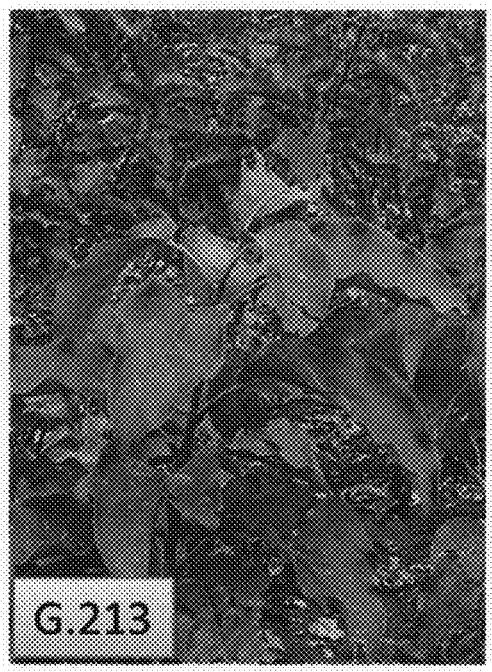
Figure 8B:
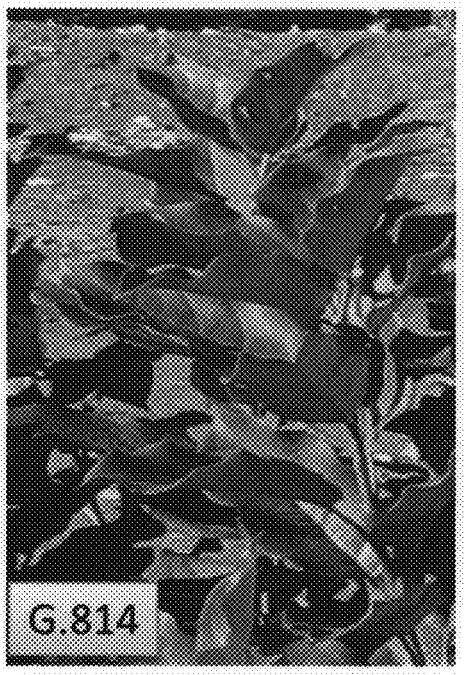
Figure 8C:
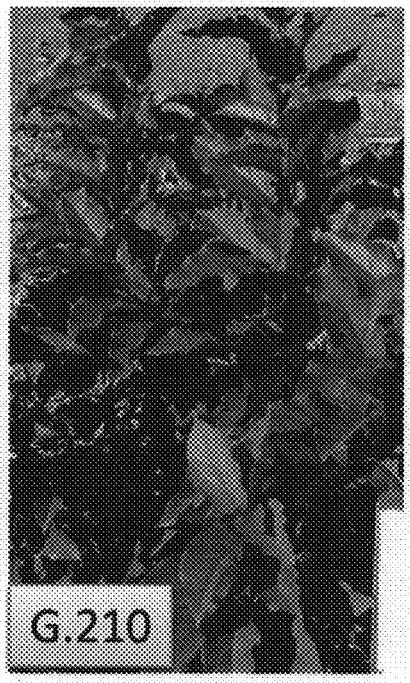
Figure 8D:
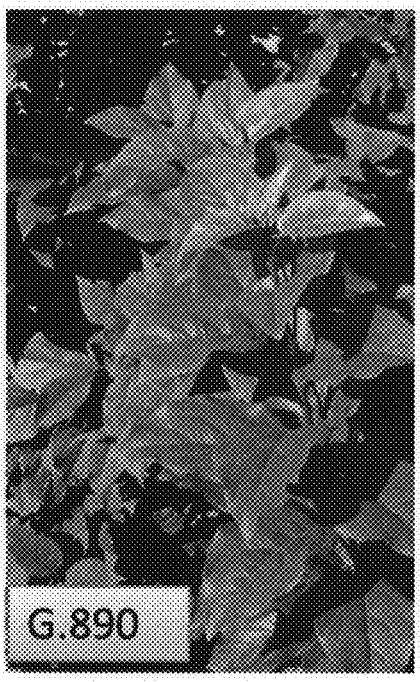
Figure 8E:
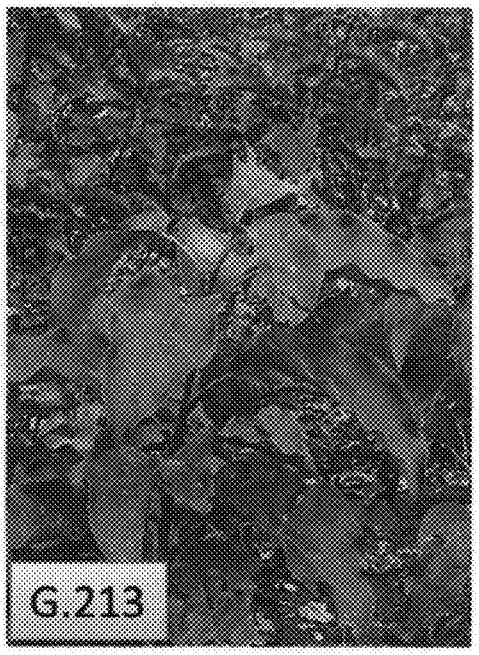
Figure 8F:
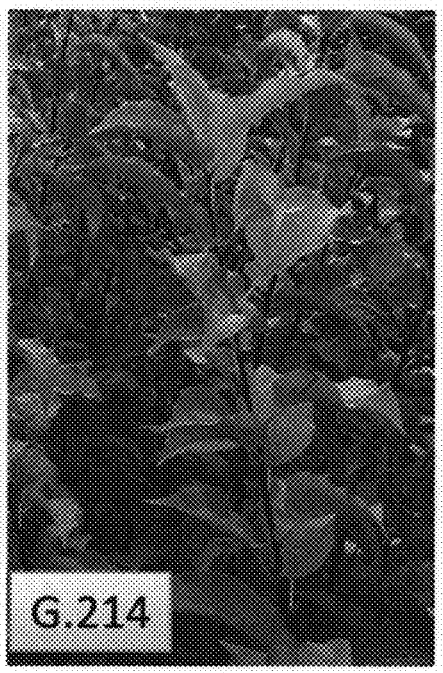
Figure 8G:
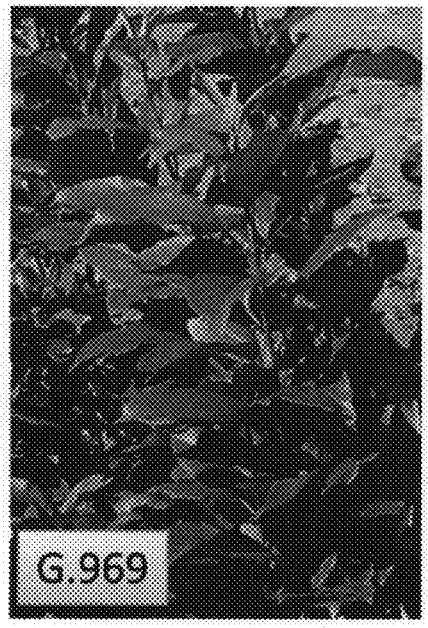
Figure 8H:
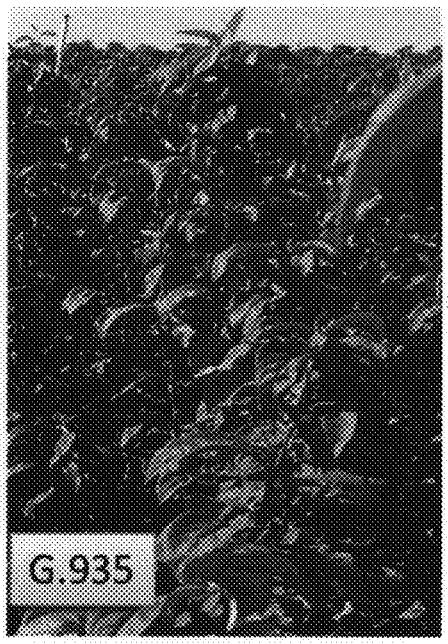

FIG. 8A to 8H show a comparison between 'G.213', 'G.814', 'G.210', 'G.890', 'G.214', 'G.969', and 'G.935'. FIG. 8A shows leaves of 'G.213'. FIG. 8B shows leaves of 'G.814'. FIG. 8C shows leaves of 'G.210'. FIG. 8D shows leaves of 'G.890'. FIG. 8E shows leaves of 'G.213'. FIG. 8F shows leaves of 'G.214'. FIG. 8G shows leaves of 'G.969'. FIG. 8H shows leaves of 'G.935'.

DETAILED BOTANICAL DESCRIPTION OF THE PLANT

The following detailed descriptions set forth the distinctive characteristics of 'G.213'. The data which define these characteristics were collected from asexual reproductions carried out in Geneva, N.Y. Color references are to The Royal Horticultural Society Colour Chart (R.H.S.), 2001 edition. Botanical descriptions follow the Manual of Cultivated Plants (Bailey, 1949). Unless otherwise specified, the botanical description of 'G.213' was taken from plants that were one year old (vegetative tissues) or eight years old (reproductive tissues).

Tree:

*Habit*.—A self-rooted tree of 'G.213' is a small shrub typically standing about 1.5-2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season.

*Productivity*.—In an intermediate trial performed in Geneva, N.Y., the 'G.213' rootstock received the cultivar 'Empire' (*Malus domestica*) as the scion and was compared to the *Malus domestica* check rootstocks 'M.9 EMLA' (not patented), 'M.26' (not patented) and 'M.7' (not patented). 'G.213' was shown to have statistically higher ($p \leq 0.05$) yield efficiency (kg yield/$cm^2$ trunk cross sectional area) than all the check rootstocks.

*Precocity*.—Scion cultivars budded on 'G.213' exhibit the same precocity as those budded on 'M.9' (not patented).

*Fertility* (*fecundity*).—The 'G.213' plant produces flowers and fruits regularly.

Dormant shoots (buds and bark):

*Dormant mature shoots*.—Color: Greyed-Orange (RHS 175C) where exposed to full sunlight grading to Greyed-Orange (RHS 173B) with diminished light exposure. Texture: Very light pubescence which gradually disappears in older tissues. Size: 30-60 cm long; may have some spines.

*Axillary buds*.—Size: 2-3 mm long and 3 mm wide with little pubescence. Shape: Obtuse, sessile, somewhat appressed and flattened. Texture: Some pubescence.

*Bark on three-year-old shoots*.—Color: Greyed-Brown (RHS 199A). Lenticels: Color: Greyed-Orange (RHS 163B). Size: 0.3-0.4 mm in diameter. Quantity: 1-2 lenticels per $cm^2$.

Leaves:

*Mature leaves*.—Leaf arrangement: Alternate. Shape: Simple, recurved, oblong-ovate. Size: Length: 95 mm. Width: 35 mm at the widest point. Laminae: Somewhat wavy. Apex: Acuminate. Base: Nearly symmetrical rounded. Margin: Acutely serrated, with about 6 serrations per cm. Upper surface: Color: Green (RHS 137C). Texture: Glabrous and translucent. Lower surface: Color: Green (RHS 147C). Texture: Somewhat pubescent. Venation: Netted. Leaf poise: 15°-25° from the shoot, depending on shoot orientation. Stipules: Color: Green (RHS 137C). Length: 8 mm. Width: 2 mm. Petioles: Diameter: 2 mm. Color: Gradation of Green (RHS 140A) to Greyed-Red (RHS 179A) depending on low or high exposure to light.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Shape: Lateral buds are obtuse, sessile, and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Size: Length: 25 mm. Width: 18 mm. Shape: Spatulate. Apex: Obtuse. Margin: Smooth. Color: Closed petals: Red (RHS 54A). Open petals: White (RHS 1550) with Red (RHS 54A), striations in some of the petals.

*Reproductive organs*.—Pistils: Length: 6 mm. Color: Yellow-white (RHS 145B). Stamens: Length: 4 mm. Color: White (RHS 155D). Anther color: Yellow-Brown (RHS 167D).

*Blooming time*.—During typical Geneva, N.Y. spring, 'G.213' has a peak bloom around May 10$^{th}$. This is similar to other rootstocks.

Fruit:

*Mature fruit*.—Size: Height: 35-40 mm. Diameter: 30-35 mm. Shape: Obloid. Color: Partial Orange skin (RHS 22A) with Red (RHS 46C) blush overtones depending on the exposure to the sun. Sepals: Persisting on a very protruding calyx. Flesh: Taste: Astringent (not meant for consumption). Color: Yellow-Orange (RHS 20C). Seed: Color: Greyed-Red (RHS 179A), translucent. Shape: Tear drop shape. Size: Length: 50-60 mm. Diameter: 25-35 mm at the widest point. Number: Generally five seeds per fruit.

Disease resistance: As described above, the 'G.213' rootstock of the present invention exhibits resistance to fire blight. The percent lesion measure after inoculation of potted liners in the greenhouse using four different strains of *E. amylovora* was negligible for two of the strains and moderate for the other two, indicating a specific resistance to the bacterium. The 'G.213' rootstock, having survived the inoculation with crown and root rot, is also considered resistant to crown and root rots caused by *Phytophthora cactorum*. 'G.213' seems to be susceptible to powdery mildew.

We claim:

1. A new and distinct variety of apple tree named 'G.213' as shown and described herein.

* * * * *